United States Patent
Rothermel et al.

(10) Patent No.: US 9,504,800 B2
(45) Date of Patent: Nov. 29, 2016

(54) HEADGEAR ATTACHMENT MECHANISM FOR A PATIENT INTERFACE DEVICE

(75) Inventors: Justin Edward Rothermel, Monroeville, PA (US); Chad Zediker, Greensburg, PA (US); Steven Charles Stegman, Gibsonia, PA (US); Christopher James Kadamus, Jamaica Plain, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 393 days.

(21) Appl. No.: 14/117,863

(22) PCT Filed: Apr. 27, 2012

(86) PCT No.: PCT/IB2012/052116
§ 371 (c)(1),
(2), (4) Date: Nov. 15, 2013

(87) PCT Pub. No.: WO2012/160458
PCT Pub. Date: Nov. 29, 2012

(65) Prior Publication Data
US 2014/0083429 A1 Mar. 27, 2014

Related U.S. Application Data

(60) Provisional application No. 61/488,318, filed on May 20, 2011.

(51) Int. Cl.
*A61M 16/00* (2006.01)
*A61M 16/08* (2006.01)
*A61M 16/06* (2006.01)

(52) U.S. Cl.
CPC ..... *A61M 16/0875* (2013.01); *A61M 16/0057* (2013.01); *A61M 16/06* (2013.01); *A61M 16/0633* (2014.02); *A61M 16/0683* (2013.01); *A61M 16/0816* (2013.01)

(58) Field of Classification Search
CPC ... A62B 18/02; A62B 18/084; A61M 16/04; A61M 16/0461; A61M 16/06; A61M 16/0605; A61M 16/0627; A61M 16/0633; A61M 16/0683; A61M 16/0694; A61M 16/0816; A61M 16/0875; A61M 25/02; A61M 2025/0213; A61M 2025/022; A61M 2025/0226; A61M 2025/0253; A61M 2025/026
USPC ............ 128/201.22–201.24, 202.27, 205.25, 128/206.21, 206.27–206.29, 207.11, 128/207.13, 207.17, 207.18, DIG. 26
See application file for complete search history.

(56) References Cited

U.S. PATENT DOCUMENTS 2,742,039 A 4/1956 Bloom
4,774,946 A * 10/1988 Ackerman ........ A61M 16/0666
104/179

(Continued)

FOREIGN PATENT DOCUMENTS

WO WO03090827 A1 11/2003

*Primary Examiner* — Tan-Uyen (Jackie) T Ho
*Assistant Examiner* — Joseph D Boecker
(74) *Attorney, Agent, or Firm* — Michael W. Haas

(57) ABSTRACT

A patient interface device includes a patient sealing assembly adapted to communicate a flow of breathing gas within an airway of a patient, a fluid coupling conduit fluidly coupled to the patient sealing assembly, the fluid coupling conduit being structured to receive the flow of breathing gas and communicate the flow of breathing gas to the patient sealing assembly, and a headgear component structured to secure the patient interface device to the patient's head, the headgear component including a strap member having a generally C-shaped connector member. The generally C-shaped connector member is structured to at least partially wrap around and be releasably received and held by or within a receiving feature provided on one of: (i) the fluid coupling conduit, and (ii) an extension member extending outwardly from the patient sealing assembly.

6 Claims, 9 Drawing Sheets

(56) References Cited

U.S. PATENT DOCUMENTS

| | | | | |
|---|---|---|---|---|
| 5,320,097 A * | 6/1994 | Clemens | ............ | A61M 16/0488 128/207.17 |
| 5,782,236 A * | 7/1998 | Ess | ................. | A61M 25/02 128/207.14 |
| 6,557,556 B2 * | 5/2003 | Kwok | ................. | A61M 16/06 128/201.24 |
| 6,612,309 B1 * | 9/2003 | Ancona | ............ | A61M 16/0465 128/207.14 |
| 7,036,508 B2 * | 5/2006 | Kwok | ................. | A61M 16/06 128/206.28 |
| 7,243,649 B2 * | 7/2007 | Moenning | ............ | A61M 16/06 128/203.12 |
| 2006/0196511 A1 * | 9/2006 | Lau | ................. | A61M 16/0666 128/207.11 |
| 2007/0068533 A1 * | 3/2007 | Bierman | ............ | A61M 16/0488 128/207.17 |
| 2008/0078396 A1 | 4/2008 | Janbakhsh | | |
| 2008/0149105 A1 * | 6/2008 | Matula | ................. | A61M 16/06 128/206.29 |
| 2008/0190432 A1 | 8/2008 | Blochlinger | | |
| 2008/0196727 A1 | 8/2008 | Ho | | |
| 2009/0044808 A1 | 2/2009 | Guney | | |
| 2010/0000545 A1 * | 1/2010 | Lee | ................. | A61M 16/0666 128/207.18 |
| 2012/0204870 A1 * | 8/2012 | McAuley | ............ | A61M 16/06 128/203.12 |

* cited by examiner

HEADGEAR ATTACHMENT MECHANISM FOR A PATIENT INTERFACE DEVICE

CROSS-REFERENCE TO RELATED APPLICATIONS

This patent application claims the priority benefit under 35 U.S.C. §371 of international patent application No. PCT/IB2012/052116, filed Apr. 27, 2012, which claims the priority benefit under 35 U.S.C. §119(e) of U.S. Provisional Application No. 61/488,318 filed on May 20, 2011, the contents of which are herein incorporated by reference.

BACKGROUND OF THE INVENTION

1. Field of the Invention

The present invention relates to respiratory therapy systems, such as non-invasive ventilation and pressure support systems, and in particular to a patient interface device for a respiratory therapy system that includes a clip mechanism that allows the headgear component of the patient interface device to be quickly and easily attached and detached from the patient sealing assembly of the patient interface device.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible cushion on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Adherence and compliance to therapy, such as CPAP or other pressure support therapies, is growing to be an industry-wide issue. Factors such as comfort and ease of a patient interface device can greatly affect a patient's adherence and compliance to therapy. Thus, more comfortable, easier to use, and/or simplified designs for patient interface devices are becoming expectations for any product that seeks to compete.

SUMMARY OF THE INVENTION

Accordingly, it is an object of the present invention to provide a patient interface device that overcomes the shortcomings of conventional patient interface devices. This object is achieved according to one embodiment of the present invention by providing a patient interface device that includes a clip mechanism that allows the headgear component of the patient interface device to be quickly and easily attached and detached from the patient sealing assembly of the patient interface device.

In one embodiment, a patient interface device is provided that includes a patient sealing assembly adapted to communicate a flow of breathing gas within an airway of a patient, a fluid coupling conduit fluidly coupled to the patient sealing assembly, the fluid coupling conduit being structured to receive the flow of breathing gas and communicate the flow of breathing gas to the patient sealing assembly, and a headgear component structured to secure the patient interface device to the patient's head, the headgear component including a strap member having a C-shaped connector member. The C-shaped connector member is structured to at least partially wrap around and be releasably received and held by or within a receiving feature provided on one of: (i) the fluid coupling conduit, and (ii) an extension member extending outwardly from the patient sealing assembly.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
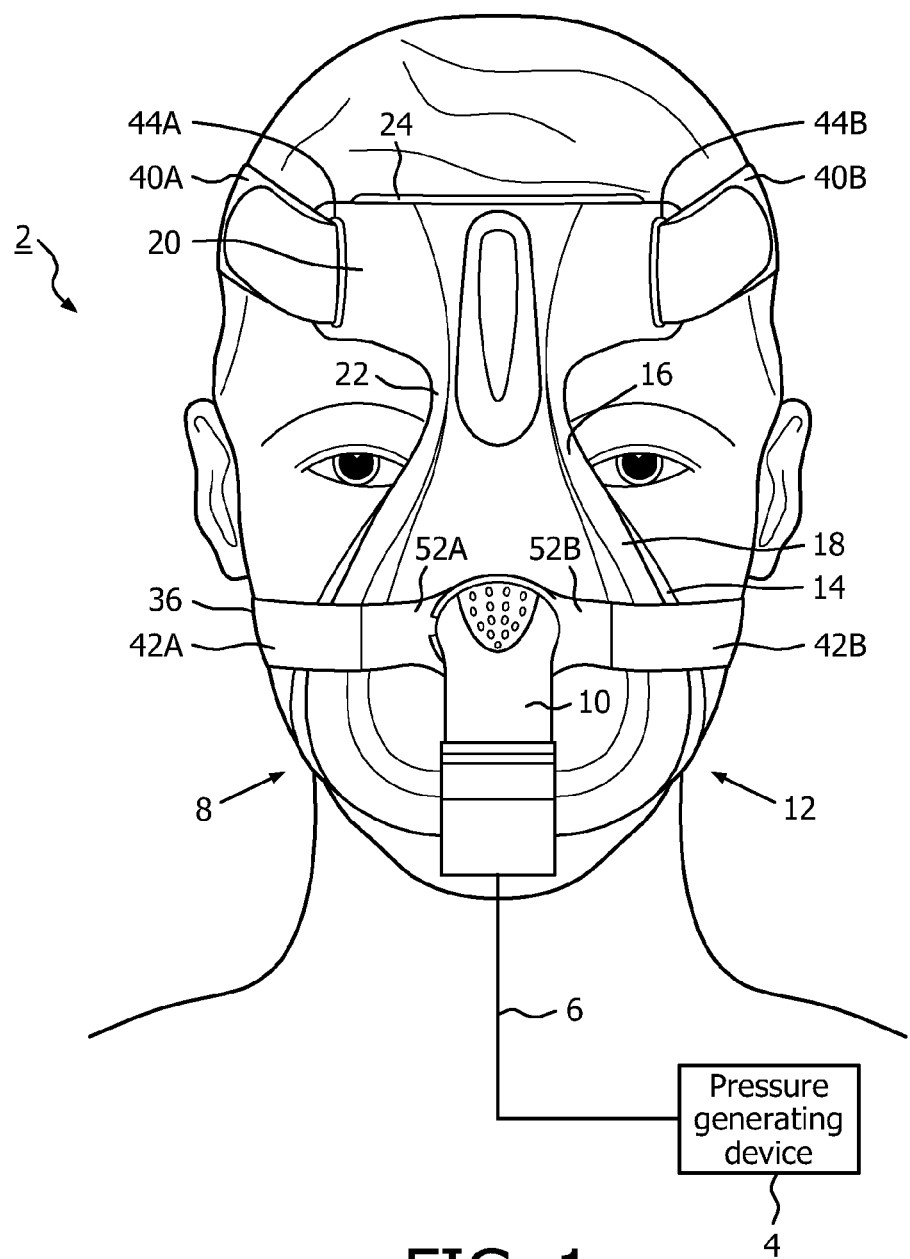
FIG. 1 is a schematic diagram of a system adapted to provide a regimen of respiratory therapy to a patient according to one exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 2 adapted to provide a regimen of respiratory therapy to a patient according to one exemplary embodiment is generally shown in FIG. 1. System 2 includes a pressure generating device 4, a patient circuit 6, and a patient interface device 8 having a fluid coupling conduit 10. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8 through fluid coupling conduit 10, which in the illustrated embodiment is an elbow connector. Delivery conduit 6 and patient interface device 8 are often collectively referred to as a patient circuit.

In the exemplary embodiment, patient interface 8 includes a patient sealing assembly 12, which in the illustrated embodiment is a nasal/oral mask. However, other types of patient sealing assemblies, such as, without limitation, a nasal mask, a nasal cushion, or a full face mask, which facilitate the delivery of the flow of breathing gas to the airway of a patient may be substituted for patient sealing assembly 12 while remaining within the scope of the present invention. Patient sealing assembly 12 includes a cushion 14 coupled to a frame member 16. In the illustrated embodiment, cushion 14 is defined from a unitary piece of soft, flexible, cushiony, elastomeric material, such as, without limitation, silicone, an appropriately soft thermoplastic elastomer, a closed cell foam, or any combination of such materials.

Also in the illustrated embodiment, frame member 16 is made of a rigid or semi-rigid material, such as, without limitation, an injection molded thermoplastic or silicone, and includes a faceplate portion 18 to which cushion 14 is fluidly attached. An opening in faceplate portion 18, to which fluid coupling conduit 10 is coupled, allows the flow of breathing gas from pressure generating device 4 to be communicated to an interior space defined by cushion 14, and then to the airway of a patient.

Frame member 16 also includes a forehead support member 20 that is coupled to the faceplate portion by a connecting member 22. A forehead cushion 24 is coupled to the rear of forehead support member 20. In the exemplary embodiment, forehead cushion 24 is made of a material that is similar to the material of cushion 14.

Figure 2:
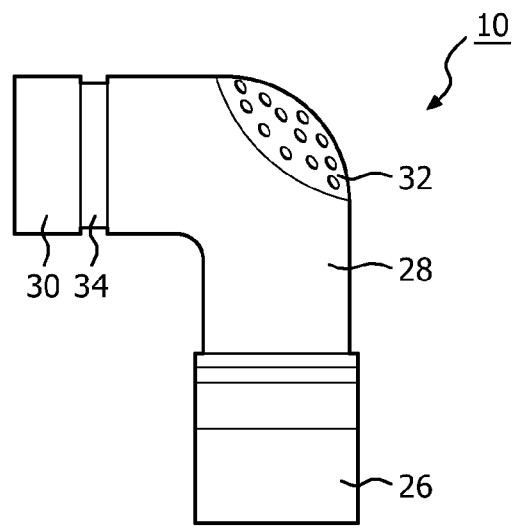
FIG. 2 is a side elevational view of a fluid coupling conduit forming a part of a patient interface device of the system shown in FIG. 1 according to one exemplary embodiment of the present invention.

FIG. 2 is a side elevational view of fluid coupling conduit 10 according to one exemplary embodiment of the present invention. Fluid coupling conduit 10 includes a first end 26, an elbow portion 28, and a second end 30. First end 26 is structured to be coupled (e.g., rotatably coupled) to delivery conduit 6, and second end 30 is structured to be coupled to faceplate portion 18. In the exemplary embodiment, an exhaust port 32 is provided in elbow portion 28 and is structured to vent gasses exhaled by the patient through patient interface device 8 to atmosphere. As seen in FIG. 2, second end 30 includes a groove 34 extending around the outer periphery thereof. The function of groove 34 is described below.

Figure 3:
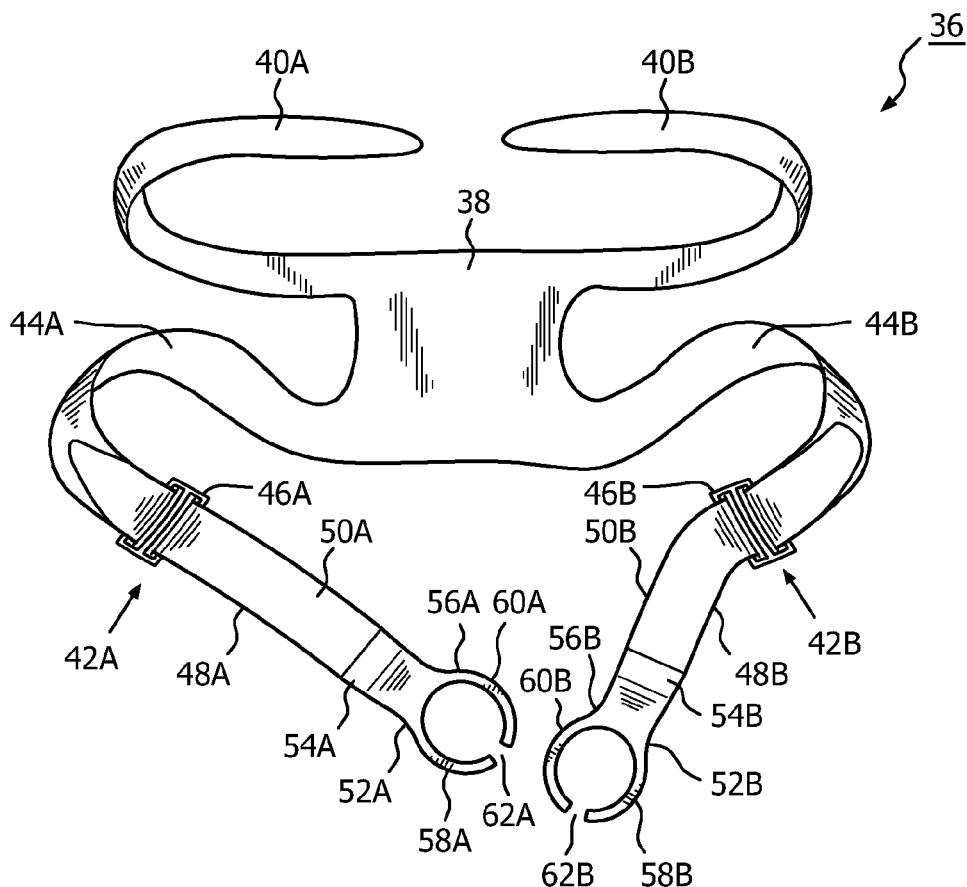
FIG. 3 is an elevational view of a headgear component forming a part of a patient interface device of the system shown in FIG. 1 according to one exemplary embodiment of the present invention.

Patient interface 8 also includes a headgear component 36 for securing patient interface device 8 to the patient's head. FIG. 3 is an elevational view of headgear component 36 according to one embodiment. Headgear component 36 includes a back member 38, upper strap members 40A, 40B, and lower strap members 42A, 42B. Upper strap members 40A, 40B extend from an upper portion of back member 38 and are structured to extend toward frame member 16 above the patient's ears as seen in FIG. 1 and be coupled to forehead support member 20. More specifically, in the exemplary embodiment, each upper strap member 40A, 40B includes a hook and loop fastening system, such as VELCRO®, provided on the end thereof. Each upper strap member 40A, 40B may thus be threaded through respective looped portions 44A, 44B provided on opposites sides of forehead support member 20 and then be bent back on itself in order to adhere the hook fastener portion to the loop fastener portion and thereby adjustably connect upper strap member 40A, 40B to forehead support member 20. It will be understood that the illustrated hook and loop fastening arrangement is meant to be exemplary only, and that other selectively adjustable fastening arrangements are also possible within the scope of the present invention.

Lower strap members 42A, 42B extend from a lower portion of back member 38 and are structured to extend toward frame member 16 below the patient's ears. As seen in FIG. 3, in the exemplary, non-limiting embodiment, each lower strap member 42A, 42B includes a respective adjustable portion 44A, 44B, looped connecting element 46A, 46B, and connector portion 48A, 48B. Each adjustable portion 44A, 44B includes a hook and loop fastening system, such as VELCRO®, provided on the end thereof, which is used to adjustably couple adjustable portion 44A, 44B the first side of the associated looped connecting element 46A, 46B. In addition, each connector portion 48A, 48B is coupled to the second side of the associated looped connecting element 46A, 46B.

Furthermore, connector portion 48A, 48B includes a strap portion 50A, 50B coupled to a C-shaped connector member 52A, 52B. In the exemplary embodiment, back member 38, upper strap members 40A, 40B, adjustable portions 44A, 44B, and strap portion 50A, 50B are made of a flexible material such as, without limitation, a fabric material like Lycra® (or another type of spandex material). Also in the exemplary embodiment, connector members 52A, 52B are made of a flexible or semi-rigid material, such as, without limitation, an injection molded thermoplastic, silicone, metal or rubber. Connector members 52A, 52B may be attached to strap portions 50A, 50B with adhesives, stitching, and/or other known manners, such as being formed as integral components.

Each connector member 52A, 52B includes a base portion 54A, 54B coupled to a C-shaped portion 56A, 56B. Each C-shaped portion 56A, 56B comprises a first arm 58A, 58B and a second arm 60A, 60B that together define a gap 62A, 62B.

When patient interface device 8 is to be donned by a patient, the patient couples upper strap members 40A, 40B to forehead support member 20 as described above. The patient then places patient interface device 8 on his or her head and positions patient sealing assembly 12 over his or her nose and mouth. Next, the patient couples lower strap members 42A, 42B to patient sealing assembly 12 by connecting each connector member 52A, 52B to fluid coupling conduit 10. In particular, the patient causes each C-shaped portion 56A, 56B to be wrapped around the second end 30 of fluid coupling conduit 10 in a manner wherein each is received within groove 34 (one stacked on top of the other). Typically, the patient will do so by applying a force to first arms 58A, 58B and second arms 60A, 60B to cause the respective gap 62A, 62B to be temporarily made wide enough to allow each C-shaped portion 56A, 56B to fit over coupling conduit 10 and be received within groove 34. When the force is removed, the C-shaped portion 56A, 56B will return to its original state and be held within groove 34.

Once lower strap members 42A, 42B are coupled to patient sealing assembly 12 as just described, the patient may selectively adjust the fit and tension of headgear component 36 by adjusting the hook and loop fastening system of either or both of upper strap members 40A, 40B and adjustable portions 44A, 44B. In addition, C-shaped portions 56A, 56B are able to rotate within groove 34, providing additional flexibility for fit and comfort. When the patient desires to remove patient interface device 8, he or she may detach lower strap members 42A, 42B from patient sealing assembly 12 by applying a pulling force to each connector portion 48A, 48B sufficient to cause the associated C-shaped portion 56A, 56B to slide out of groove 34 and be pulled away from fluid coupling conduit 10.

Connector portions 48A, 48B of lower strap members 42A, 42B thus provide a simple and easy to use mechanism for attaching and detaching headgear component 38 to and from patient sealing assembly 12.

Figure 4:
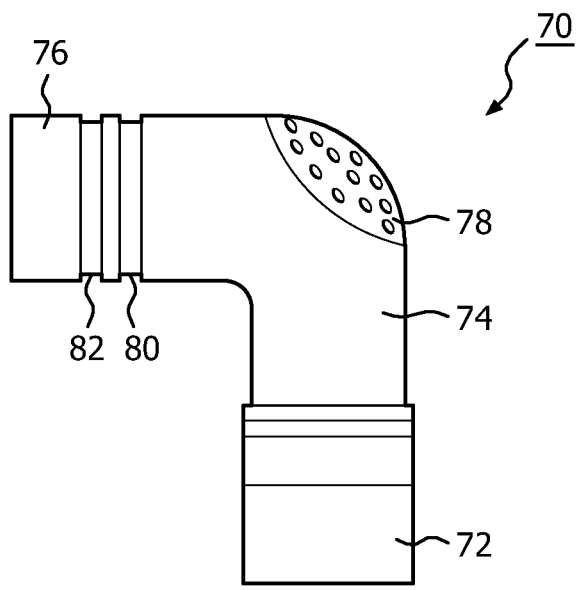
FIG. 4 is a side elevational view of a fluid coupling conduit forming a part of a patient interface device of the system shown in FIG. 1 according to an alternative exemplary embodiment of the present invention.

FIG. 4 is a side elevational view of a fluid coupling conduit 70 according to an alternative exemplary embodiment of the present invention that may be substituted for fluid coupling conduit 10. Fluid coupling conduit 70 includes a first end 72, an elbow portion 74, and a second end 76. First end 72 is structured to be coupled (e.g., rotatably coupled) to delivery conduit 6, and second end 76 is structured to be coupled to faceplate portion 18. In the exemplary embodiment, an exhaust port 78 is provided in elbow portion 74 and is structured to vent gasses exhaled by the patient through patient interface device 8 to atmosphere. In addition, as seen in FIG. 4, second end 76 includes a first groove 80 and a second groove 82 each extending around the outer periphery thereof. In this embodiment, first groove 80 is structured to receive one of the C-shaped portions 56A, 56B and second groove 82 is structured to receive the other of the C-shaped portions 56A, 56B.

Figure 5:
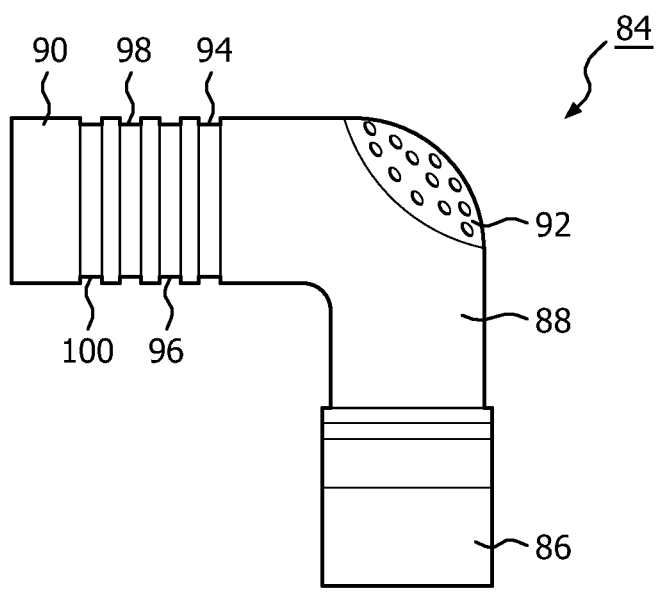
FIG. 5 is a side elevational view of a fluid coupling conduit forming a part of a patient interface device of the system shown in FIG. 1 according to another alternative exemplary embodiment of the present invention.

FIG. 5 is a side elevational view of a fluid coupling conduit 84 according to another alternative exemplary embodiment of the present invention that may be substituted for fluid coupling conduit 10. Fluid coupling conduit 84 includes a first end 86, an elbow portion 88, and a second end 90. First end 86 is structured to be coupled (e.g., rotatably coupled) to delivery conduit 6, and second end 90 is structured to be coupled to faceplate portion 18. In the exemplary embodiment, an exhaust port 92 is provided in elbow portion 74 and is structured to vent gasses exhaled by the patient through patient interface device 8 to atmosphere. In addition, as seen in FIG. 5, second end 76 includes a first groove 94, a second groove 96, a third groove 98 and a fourth groove 100 each extending around the outer periphery thereof. In this embodiment, the C-shaped portions 56A, 56B may together be inserted into any one of first groove 94, second groove 96, third groove 98 and fourth groove 100. The particular groove 94, 96, 98, 100 that is employed will affect the fit of lower strap members 42A, 42B on the patient, thus providing an easy to use adjustment mechanism for the patient. Although four grooves are shown in FIG. 5, more or less groove may also be employed within the scope of her present invention. In addition, in this embodiment, the connector portions 48A, 48B may be individually inserted into different ones of the grooves 94, 96, 98, 100.

Figure 6:
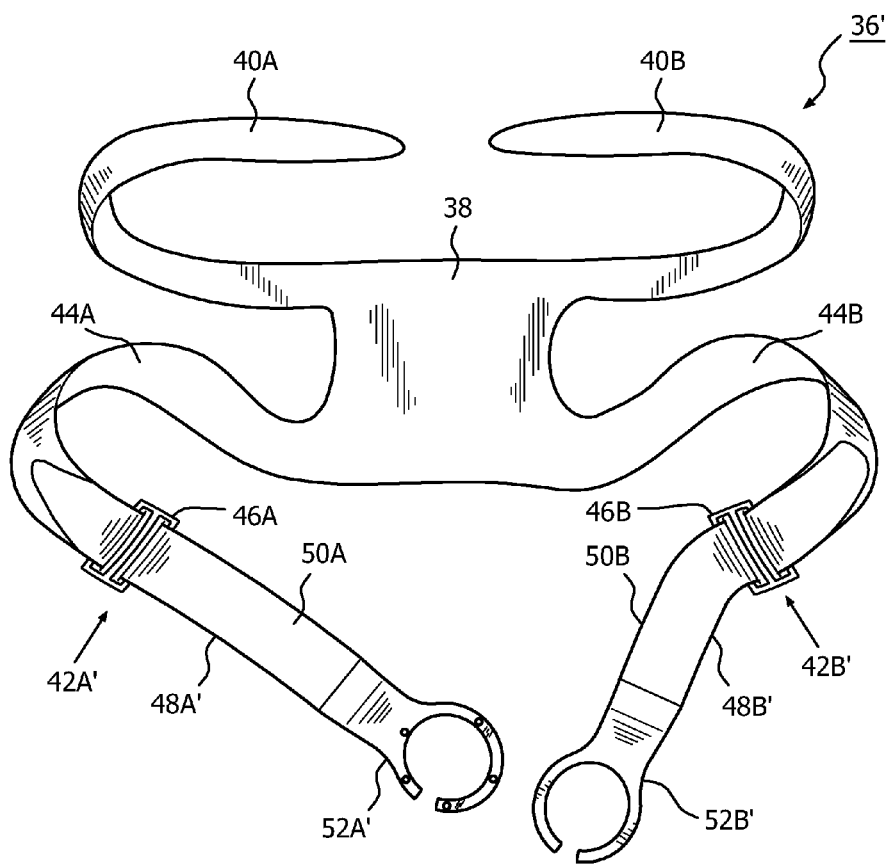
FIG. 6 is an elevational view of a headgear component forming a part of a patient interface device of the system shown in FIG. 1 according to an alternative exemplary embodiment of the present invention.

FIG. 6 is an elevational view of a headgear component 36' according to an alternative embodiment of the present invention. Headgear component 36' may be substituted for headgear component 36 and includes a number of the same components. Like components are thus labeled with like reference numerals. Headgear component 36', however, includes alternative lower strap members 42A', 42B' having alternative connector portions 48A', 48B'. Alternative connector portions 48A', 48B' each have an alternative connector member 52A', 52B' that, as described below, are able to be coupled to one another before being coupled to fluid coupling conduit 10.

Figure 7:
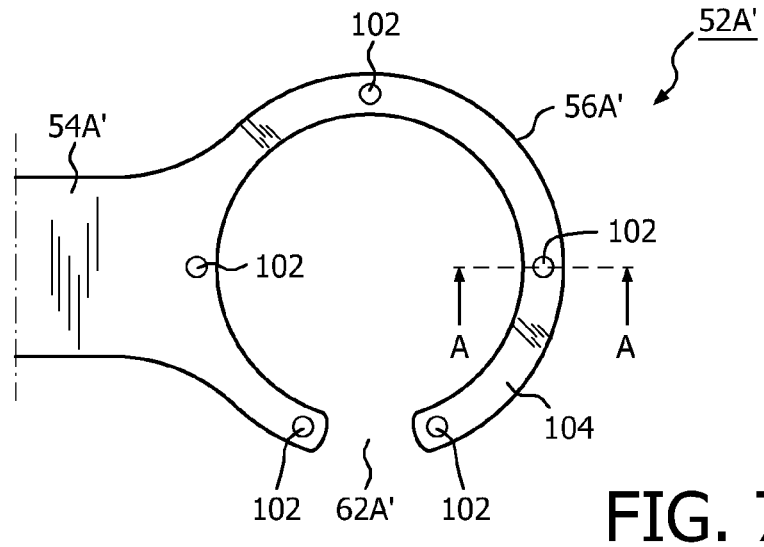
FIG. 7 is a top plan view of a first connector member and FIG. 8 is a bottom plan view of second connector member of the headgear component of FIG. 6.

FIG. 7 is a top plan view of connector member 52A'. Connector member 52A' includes a base portion 54A' coupled to a C-shaped portion 56A', wherein a gap 62A' is provided at the bottom of C-shaped portion 56A' such that the gap 62A' is centered at a location around C-shaped portion 56A' that is about 90 degrees from the center of base portion 54A' (i.e., the longitudinal axis of base portion 54A'). This is in contrast to gap 62A of connector member 52A which is centered at a location around C-shaped portion 56A that is about 180 degrees from the center of base portion 54A (in other words, it is directly across from the center of base portion 54A). In addition, a plurality of pegs 102 are provided on and extend upwardly from the top surface 104 of C-shaped portion 56A'.

Figure 8:
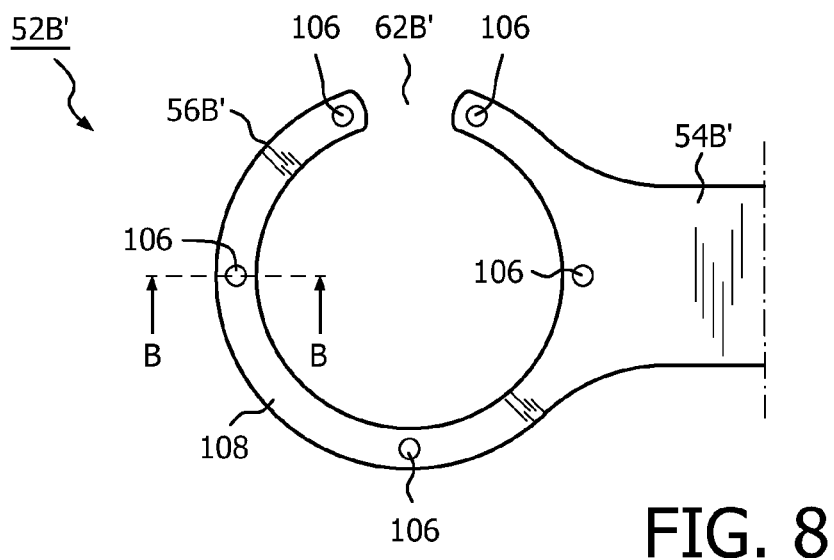

FIG. 8 is a bottom plan view of connector member 52B'. Connector member 52B' includes a base portion 54B' coupled to a C-shaped portion 56B', wherein a gap 62B' is provided at the bottom of C-shaped portion 56A' such that the gap 62B' is centered at a location around C-shaped portion 56B' that is about 90 degrees from the center of base portion 54B' (i.e., the longitudinal axis of base portion 54B'). This is in contrast to gap 62B of connector member 52B which is centered at a location around C-shaped portion 56B that is about 180 degrees from the center of base portion 54B (in other words, it is directly across from the center of base portion 54B). In addition, a plurality of holes 106, each structured and positioned to receive a respective peg 102, are provided in the bottom surface 104 of C-shaped portion 56B'.

Figure 9:
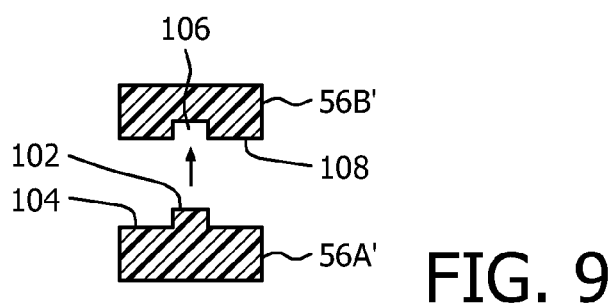
FIG. 9 provides cross-sectional views of the connector members of FIGS. 7 and 8.
Figure 10:
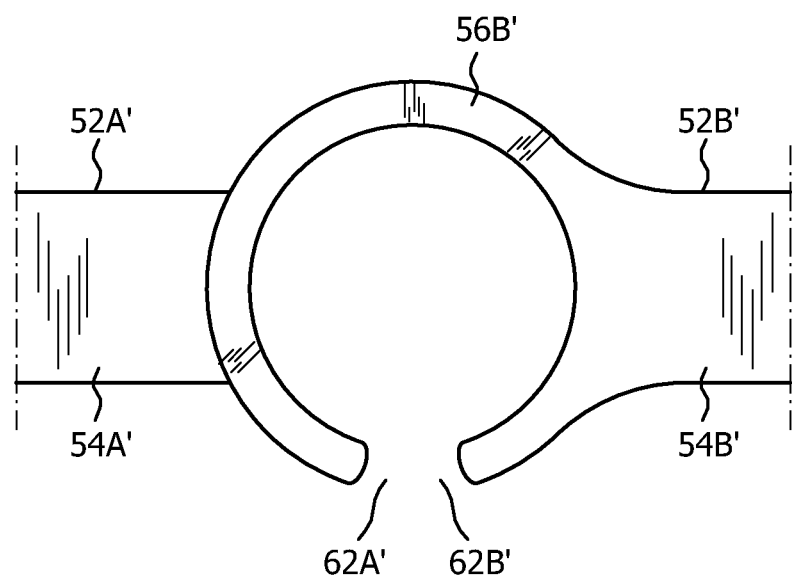
FIG. 10 is a top plan view showing the connector members of FIGS. 7 and 8 attached to one another according to one embodiment.

In order to connect connector member 52A' to connector member 52B', connector member 52B' is placed on top of connector member 52A' in a manner wherein bottom surface 108 faces top surface 104. Each peg 102 is then inserted into a respective hole 106, as shown in FIG. 9 (which shows a cross-sectional view of connector member 52A' taken along lines A-A of FIG. 7 and a cross-sectional view of connector member 52B' taken along lines B-B of FIG. 8) to secure the two parts together. FIG. 10 is a top plan view showing connector member 52A' connected to connector member 52B' in this manner When patient interface device 8 employing headgear component 36' is to be donned by a patient, the patient couples upper strap members 40A, 40B to forehead support member 20 as described elsewhere herein. The patient then places patient interface device 8 on his or her head and positions patient sealing assembly 12 over his or her nose and mouth. Next, the patient couples lower strap members 42A', 42B' to patient sealing assembly 12 by connecting the connector members 52A', 52B' (as shown in FIG. 10) to fluid coupling conduit 10. In particular, the patient causes the aligned and connected C-shaped portions 56A', 56B' to be wrapped around the second end 30 of fluid coupling conduit 10 and received within groove 34. Typically, the patient will do so by applying a force to the aligned and connected C-shaped portions 56A', 56B' sufficient to cause the aligned gaps 62A', 62B' to be temporarily made wide enough to allow the C-shaped portions 56A', 56B' to fit over coupling conduit 10 and be received within groove 34. When the force is removed, the aligned and connected C-shaped portions 56A', 56B' will return to their original states and be held within groove 34.

Once lower strap members 42A', 42B' are coupled to patient sealing assembly 12 as just described, the patient may selectively adjust the fit and tension of headgear component 36' by adjusting the hook and loop fastening system of either or both of upper strap members 40A, 40B and adjustable portions 44A, 44B. When the patient desires to remove patient interface device 8, he or she may detach the joined lower strap members 42A', 42B' from patient sealing assembly 12 simultaneously by simply applying a pulling force to the connected C-shaped portions 56A', 56B' sufficient to cause them to together slide out of groove 34 and be pulled away from fluid coupling conduit 10. Headgear component 36' may also be used with fluid coupling conduit 84 to provide the additional fit adjustment functionality described elsewhere herein.

Figure 11:
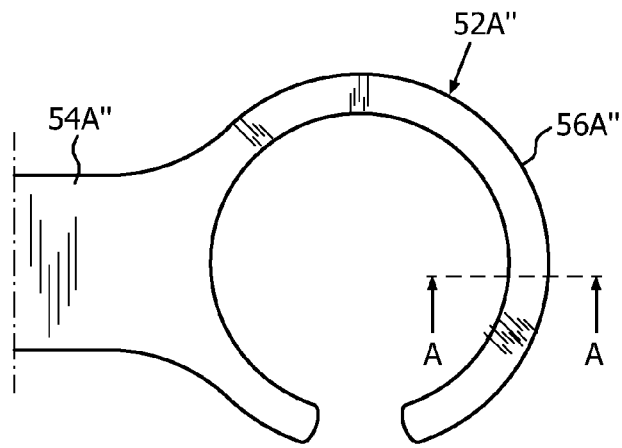
FIG. 11 is a top plan view of a first connector member and FIG. 12 is a bottom plan view of second connector member according to a further alternative embodiment.
Figure 12:
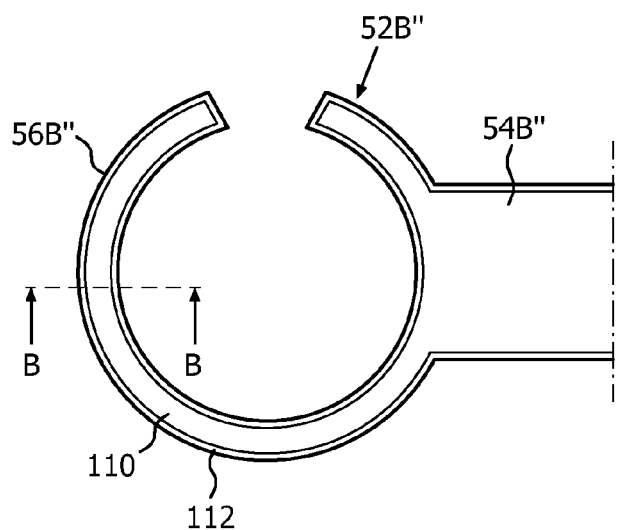
Figure 13:
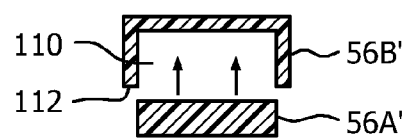
FIG. 13 provides cross-sectional views of the connector members of FIGS. 11 and 12.

FIG. 11 is a top plan view of a connector member 52A" and FIG. 12 is a bottom plan view of a connector member 52B" according to a further alternative embodiment. Connector members 52A", 52B" may be substituted for connector members 52A', 52B' in headgear component 36'. Connector members 52A" and 52B" each include a base portion 54A", 54B" coupled to a C-shaped portion 56A", 56B", wherein a gap 62A", 62B" is provided at the bottom of C-shaped portion 56A", 56B" such that each gap 62A", 62B" is centered at a location around the associated C-shaped portion 56A", 56B" that is about 90 degrees from the center of the associated base portion 54A", 54B" (i.e., the longitudinal axis of base portion 54A", 54B"). In addition, a groove 110 is provided in the bottom surface 112 of connector member 52B" which is sized and structured to receive connector member 52A" as shown in FIG. 13 (which shows a cross-sectional view of connector member 52A" taken along lines A-A of FIG. 11 and a cross-sectional view of connector member 52B" taken along lines B-B of FIG. 12) to enable the two components to be nested and connected to one another.

Figure 14:
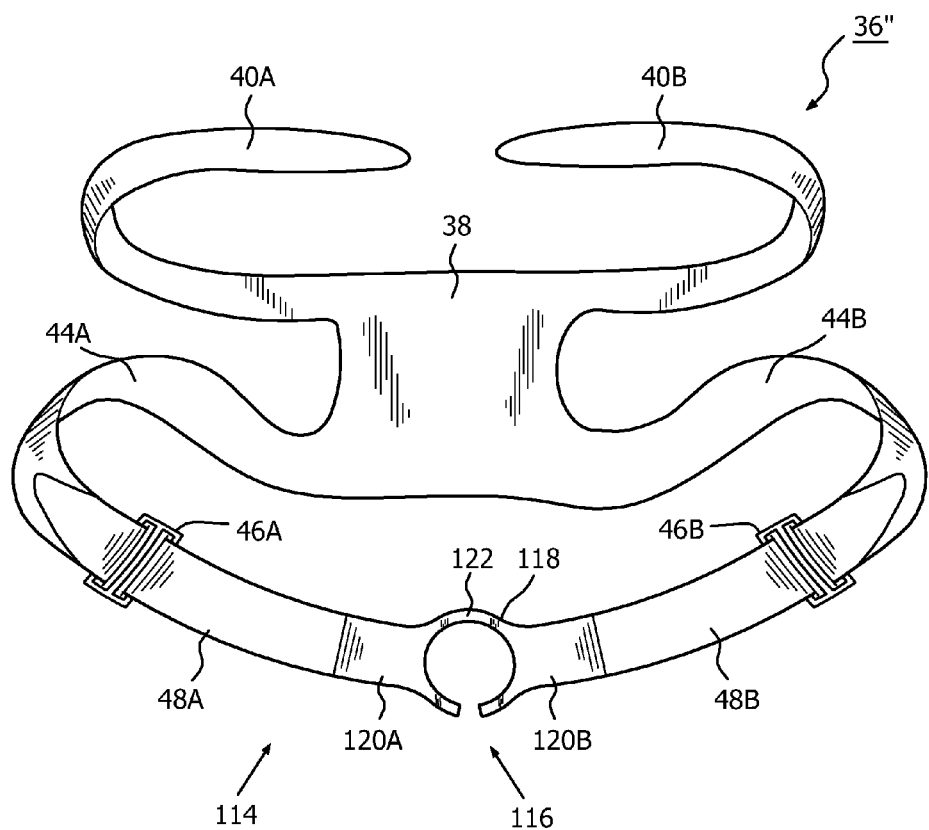
FIG. 14 is an elevational view of a headgear component forming a part of a patient interface device of the system shown in FIG. 1 according to another alternative exemplary embodiment of the present invention.

FIG. 14 is an elevational view of a headgear component 36" according to a further alternative embodiment of the present invention. Headgear component 36" may be substituted for headgear component 36 and includes a number of the same components. Like components are thus labeled with like reference numerals. Headgear component 36", however, includes an alternative lower strap member 114. Lower strap member 114 includes an attachment member 116 that includes connector members 48A, 48B as described elsewhere herein, each being attached to a central C-shaped connector member 118. Central C-shaped connector member 118 includes first and second base portions 120A, 120B coupled to a single C-shaped portion 122. Central C-shaped connector member 118 is thus able to be attached to and detached from fluid coupling conduit 10 or fluid coupling conduit 84 in the same manner as the aligned and connected C-shaped portions 56A', 56B' (FIG. 10) described elsewhere herein.

Figure 15:
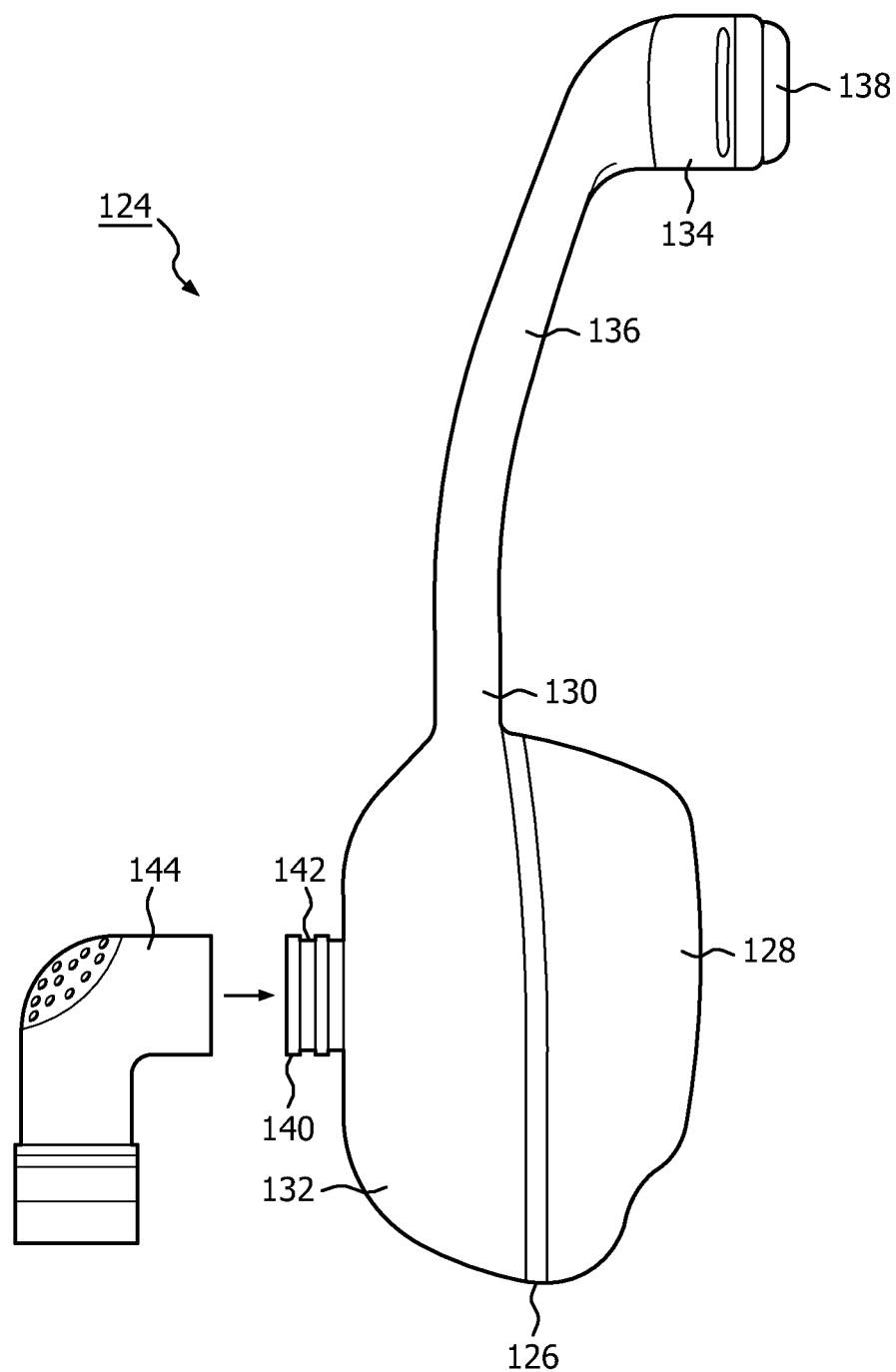
FIG. 15 is a side elevational view of a patient interface device according to a further alternative embodiment of the invention.

FIG. 15 is a side elevational view of a patient interface device 124 according to a further alternative embodiment of the invention. Patient interface device 124 includes a patient sealing assembly 126, which in the illustrated embodiment is a nasal/oral mask. However, other types of patient sealing assemblies, such as, without limitation, a nasal mask, a nasal cushion, or a full face mask, which facilitate the delivery of the flow of breathing gas to the airway of a patient may be substituted for patient sealing assembly 126 while remaining within the scope of the present invention. Patient sealing assembly 126 includes a cushion 128 coupled to a frame member 130. Frame member 130 includes a faceplate portion 132 to which cushion 128 is fluidly attached. Frame member 130 also includes a forehead support member 134 that is coupled to faceplate portion 132 by a connecting member 136. A forehead cushion 138 is coupled to the rear of forehead support member 134.

A connecting member 140 having a groove 142 extends outwardly from faceplate portion 18. Connecting member 140 is structured to receive fluid coupling conduit 144, which in the illustrated embodiment is an elbow connector, to allow the flow of breathing gas from a pressure generating device (e.g., pressure generating device 4) to be communicated to an interior space defined by cushion 128, and then to the airway of a patient. In addition, any of the headgear component embodiments described above may be coupled to connecting member 140 in groove 142 in the manner described in detail elsewhere herein for the purpose of securing patient interface device 124 to the head of the patient. Furthermore, connecting member 140 may have additional grooves like fluid coupling conduits 70 and 84 described elsewhere herein.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device, comprising:
    a patient sealing assembly adapted to communicate a flow of breathing gas within an airway of a patient;
    a fluid coupling conduit fluidly coupled to the patient sealing assembly, the fluid coupling conduit being structured to receive the flow of breathing gas and communicate the flow of breathing gas to the patient sealing assembly along a longitudinal axis of the fluid coupling conduit; and
    a headgear component structured to secure the patient interface device to the patient's head, the headgear component including a strap member having a generally C-shaped connector member and a second strap member having a second generally C-shaped connector member, the generally C-shaped connector member and the second generally C-shaped connector member both being structured to at least partially wrap around and be releasably received and held within a groove provided in one of: (i) the fluid coupling conduit, and (ii) an extension member in fluid communication with the fluid coupling conduit and extending outwardly from the patient sealing assembly, wherein when the generally C-shaped connector member and the second generally C-shaped connector member are received in the groove the generally C-shaped connector member and the second generally C-shaped connector member are rotatable about the longitudinal axis of the fluid coupling conduit, wherein the C-shaped connector member is structured to wrap around a first side of the patient's head and the second C-shaped connector member is structured to wrap around second side of the patient's head when the patient interface device is donned by the patient, wherein the C-shaped connector member has a first base portion coupled to a first C-shaped portion, and a first gap provided between a first terminal end and a second terminal end of the first C-shaped portion such that the first gap is centered at a location around the first C-shaped portion that is about 90 degrees from a center point of the first base portion that is located along a longitudinal axis of the first base portion, wherein the second C-shaped connector member has a second base portion coupled to a second C-shaped portion, and a second gap provided between a first terminal end and a second terminal end of the second C-shaped portion such that the second gap is centered at a location around the second C-shaped portion that is about 90 degrees from a center point of the second base portion that is located along a longitudinal axis of the second base portion, wherein the C-shaped connector member and the second C-shaped connector member are structured to be releasably connected to one another to form a coupled connector in a manner wherein the first gap overlaps the second gap, and wherein the coupled connector is structured to at least partially wrap around and be releasably received and held by or within the groove.

2. The patient interface device according to claim 1, wherein the patient sealing assembly comprises a cushion and a frame member coupled to the cushion, the frame member having a faceplate portion, and wherein the extension member extends outwardly from the faceplate portion.

3. The patient interface device according to claim 1, wherein the groove is provided on the extension member, and wherein the fluid coupling conduit is fluidly coupled to the extension member.

4. The patient interface device according to claim 1, wherein the groove is provided on the fluid coupling conduit.

5. The patient interface device according to claim 1, wherein a first surface of the C-shaped connector member has a plurality of pegs and a second surface of the second C-shaped connector member has a plurality of holes, and wherein each of the pegs is received within a respective one of the holes when the C-shaped connector member and the second C-shaped connector member are connected to one another.

6. The patient interface device according to claim 1, wherein a first surface of the C-shaped connector member has a coupling groove, and wherein the second C-shaped connector member is structured to be received within the coupling groove when the C-shaped connector member and the second C-shaped connector member are connected to one another in a nesting fashion.

* * * * *